United States Patent [19]

Smith

[11] Patent Number: 4,646,741

[45] Date of Patent: Mar. 3, 1987

[54] SURGICAL FASTENER MADE FROM POLYMERIC BLENDS

[75] Inventor: Carl R. Smith, Bloomingdale, N.J.

[73] Assignee: Ethicon, Inc., Somerville, N.J.

[21] Appl. No.: 670,105

[22] Filed: Nov. 9, 1984

[51] Int. Cl.$^4$ .................. A61B 17/08; A61B 17/04
[52] U.S. Cl. .................. 128/334 R; 128/334 C; 128/335.5; 128/326; 525/411
[58] Field of Search ............ 525/411; 128/334, 334 C, 128/335.5, 326

[56] References Cited

U.S. PATENT DOCUMENTS

| | | | |
|---|---|---|---|
| 3,636,956 | 1/1972 | Schneider | 128/335.5 |
| 4,052,988 | 10/1977 | Doddi et al. | 528/354 |
| 4,201,216 | 5/1980 | Mattei | 128/335.5 |
| 4,402,445 | 9/1983 | Green | 128/334 R |
| 4,428,376 | 1/1984 | Mericle | 128/335 |

Primary Examiner—Veronica P. Hoke
Attorney, Agent, or Firm—Charles J. Metz

[57] ABSTRACT

A surgical fastener is made from a blend of a lactide/glycolide copolymer and poly(p-dioxanone).

8 Claims, 10 Drawing Figures ized, and shortening the operating room time.
SURGICAL FASTENER MADE FROM POLYMERIC BLENDS The invention relates to an absorbable surgical fastener such as a ligating clip or a surgical staple of the fastener/receiver type, made from blends of polymers.

BACKGROUND OF THE INVENTION

Surgical staples and ligating clips are beginning to come into wide use in the surgical profession as an alternative to sutures and ligatures. One advantage of clips and staples in comparison with sutures and ligatures is that tissue fastening or ligating with a staple or clip, whether applied singly or as an array applied in a row or in a ring, is much simpler and faster than with a suture or a ligature. Surgical procedures can be speeded up, thereby reducing the length of time the patient must be anesthetized and shortening the operating room time. Thus, there are both medical and economic reasons for the shift to staples and clips from sutures and ligatures.

The first surgical staples to be used, and still the majority being used, were metal staples. But metal staples, when used externally, must be removed, with accompanying patient discomfort. And when metal staples are used internally, they are left in place. While the metal staples are tiny and become encapsulated by natural processes, and little or no difficulty has been associated with such staples left in the patient, for internal applications surgeons would prefer to use absorbable materials that eventually disappear after their usefulness has ended. For this reason, there is a substantial incentive to develop an absorbable plastic surgical staple.

It appears to be out of the question to produce an absorbable plastic surgical staple of reasonable size that fastens simply by bending back on itself in a manner analogous to the way metal staples fasten. The available absorbable plastics simply lack the required combination of ductility and stiffness that would be required for this purpose. For this reason, the initial attempts to produce an acceptable absorbable plastic surgical staple has concentrated on the fastener/receiver type of staple. In this type of staple, a fastener member includes a base and one or more attached legs which are designed to pierce the tissue to be fastened and to enter receptacles in the receiver on the other side of the tissue. The receiver holds the legs tightly, with the tissue being held between the fastener member and the receiving member. The desirable characteristics of such a staple are the following:

(1) adequate stiffness in the legs to pierce the tissue without being deflected in such a way that they fail to meet the receptacles in the receiver;

(2) adequate strength in the receiver to hold the legs;

(3) strength retention in situ for a period which may vary from about three to six weeks, depending on the function of the staple;

(4) dimensional stability at moderately elevated temperatures, e.g., up to 85° C.;

(5) sterilizability; and (6) ability to be totally absorbed within a reasonable period of time.

It has not proven to be an easy matter to obtain the requisite combination of properties. For instance, early designs of absorbable surgical staples utilized temporary metal reinforcement for the fastener legs during insertion of the staple to insure adequate stiffness. For instance, see Noiles, U.S. Pat. No. 4,060,089 and Green, U.S. Pat. No. 4,402,445. A presently commercial absorbable clip and an early commercial absorbable staple are made from an 80/20 lactide/glycolide (mol/mol) copolymer. These fasteners have the disadvantage that they are dimensionally unstable when heated to temperatures over 120° F. (49° C.). Therefore, care must be taken in handling these fasteners, because temperatures well over 120° F. are commonly encountered in shipping and storage in the United States during the warmer months.

A later commercial surgical staple is made from a mixture of a lactide/glycolide copolymer (85/15 molar ratio) plus another polymer that is either a homopolymer of glycolide or a 50/50 glycolide/lactide copolymer.

Absorbable ligating clips made from poly(p-dioxanone) have recently been introduced commercially. Metallic ligating clips have been used for some time.

This invention provides an absorbable surgical fastener, such as a surgical staple, a ligating clip, an anastomotic coupler, a fascia closure, or the like, that has an excellent combination of properties.

BRIEF SUMMARY OF THE INVENTION

This invention provides a surgical fastener comprising a blend of a lactide/glycolide copolymer and poly(p-dioxanone). In one preferred aspect the invention provides a surgical staple comprising:

(a) a fastener member including a base member and at least one pointed leg member extending substantially perpendicularly from said base member; and (b) a receiving member including an aperture arranged and constructed to receive and retain the free end of said leg member, wherein said fastener member comprises a blend of (a) a copolymer containing from about 65 to about 90 mole percent lactide and from about 10 to about 35 mole percent glycolide, and (b) from about 25 to about 50 weight percent poly(p-dioxanone), and wherein said receiving member comprises an absorbable polymer, preferably poly(p-dioxanone).

In another aspect, the invention provides a ligating clip comprising said blend.

THE PRIOR ART

Green, in U.S. Pat. No. 4,402,445, discloses absorbable surgical staples made from, inter alia, "an amorphous copolymer of 10–50% (by weight) glycolide and 50–90% lactide..." and from "... polymers of p-dioxanone..." Noiles, in U.S. Pat. No. 4,060,089, discloses the preparation of surgical staples from polyglycolic acid and polylactic acid.

Mericle, in U.S. Pat. No. 4,428,376, discloses the preparation of surgical staples from homopolymers and copolymers of lactide, glycolide, and p-dioxanone.

Golden et al., in United States patent application Ser. No. 359,443, filed Mar. 18, 1982 discloses an absorbable staple in which the fastening member is made from "an absorbable polymer of glycolide and lactide" and the receiving member is made from polydioxanone. The said Golden et al. application is assigned to the same assignee as this application.

Doddi et al., in U.S. Pat. No. 4,052,988, disclose surgical devices made from poly(p-dioxanone).

RELEVANT PUBLICATION

World patent application WO8401-508-A describes absorbable surgical fasteners made from copolymers containing 70-85 mole percent lactide and 15-30 mole percent glycolide.

DETAILED DESCRIPTION OF THE INVENTION

Figure 1:
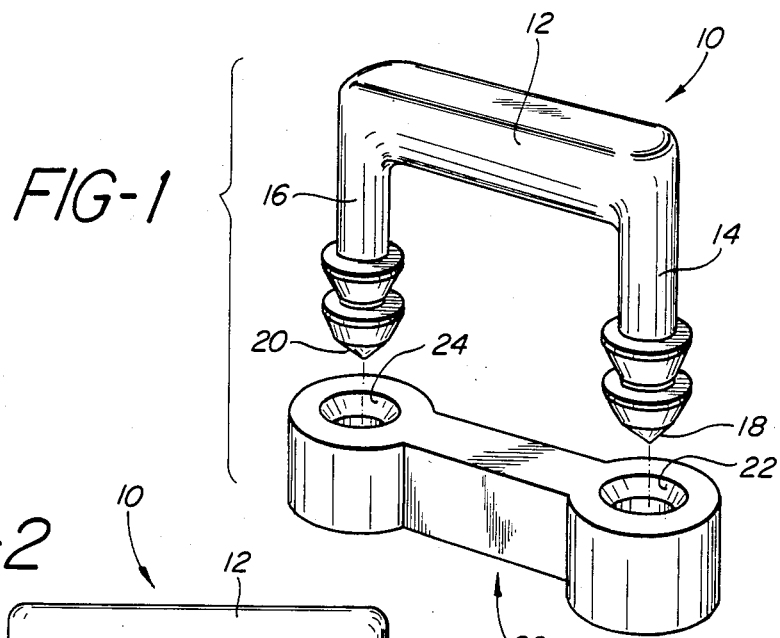
FIG. 1 is an exploded perspective view of a fastener/receiver type surgical staple useful in the invention.

The invention resides in the use in a surgical fastener of a blend of two polymers, a lactide/glycolide copolymer and poly(p-dioxanone). The blend used is a melt blend, that is, the two polymers are blended in the melt.

The copolymer employed in the invention is one that is made from a mixture of from about 65 to about 90 mole percent lactide and from about 10 to about 35 mole percent glycolide. The preferred copolymer is an 85/15 lactide/glycolide (mole percent) copolymer. The lactide/glycolide copolymers used in the invention are known materials. For instance, they are disclosed in United States patents to Schneider (U.S. Pat. No. 2,703,316), Salzberg (U.S. Pat. No. 2,758,987), Trehu (U.S. Pat. No. 3,531,561), and Wasserman et al. (U.S. Pat. No. 3,839,297). An injection molding grade of the copolymer is used. As a rule, the copolymer will have a molecular weight such that it has an inherent viscosity of from about 1 to about 3 and preferably about 1.6 to 1.9, dl/gm, tested at 25° C. at a concentration of 0.1 gm/dl in hexafluoroisopropyl alcohol ("HFIP").

Poly(p-dioxanone) is also a known material. Its nature and preparation are described, for instance, in Doddi et al., U.S. Pat. No. 4,052,988. Poly(p-dioxanone) having an inherent viscosity of from about 1.2 to about 2.2, and preferably about 1.6 to 1.9, dl/gm, tested at 25° C. and a concentration of 0.1 gm/dl in HFIP, is normally used in the invention.

The copolymer is preferably used in the blend in a major amount, usually in the proportions of from over 50 to about 75 weight percent, the remainder comprising poly(p-dioxanone).

The proportions indicated above, while not narrowly critical, are important for obtaining a number of the desirable properties of the fastener of the invention. For instance, with respect to the lactide/glycolide copolymer, if the proportion of lactide were too high the absorption time of the fastener would be too long and if the glycolide proportion were too high the breaking strength retention upon implantation in the body would be too short. With respect to the proportion of poly(p-dioxanone) in the blend, if the proportion were too high the fastener would have inadequate stiffness and if it were too low the dimensional stability upon exposure to elevated temperature would be inadequate.

In one preferred aspect, the invention provides a surgical staple of the fastener/receiver type wherein the fastener member is the blend of the invention and the receiver is an absorbable polymer, preferably poly(p-dioxanone). With respect to the use of the blend in the fastener member, the principal advantages that are obtained by the addition of poly(p-dioxanone) to the copolymer are improved heat resistance so that dimensional change upon exposure to moderately elevated temperature (e.g. 120° to 185° F.) is less apt to occur, and slightly reduced absorption time upon implantation in the body, while still maintaining acceptable breaking strength retention after implantation. (The improvements are with respect to fastener members made from the said copolymer alone.)

The receiver member is preferably made from poly(p-dioxanone) of the same grade and molecular weight indicated above for use in the fastener member.

The staple can be made by injection molding of the two parts of the staple. The fastener member, which is made of a blend of a lactide/glycolide copolymer and poly(p-dioxanone), can be injection molded at temperatures within the range of from about 130° C. to about 140° C. at an injection molding pressure of, for example, 1650 to 1750 psi. Typically, the feed for the injection molder will be a melt blend of the two polymers in pellet form, as is more specifically illustrated below in the Examples. The receiving member, made of poly(p-dioxanone), can be injection molded at a temperature within the range of from about 105° C. to about 120° C., at a pressure of, for example, about 1350 to 1450 psi. The polymers should be quite dry when being injection molded in order to avoid hydrolytic degradation during processing. After molding, the staple can be packaged and sterilized with ethylene oxide or by gamma radiation by conventional procedures.

It is recommended that the polymers be handled so as to minimize premature hydrolytic degradation or thermal degradation. Thus, the polymers should be stored dry before molding, the molding operation should be dry, and the molded parts should be stored dry. Also, residence time in the extruder should be kept to a minimum so as to minimize thermal and shear degradation. These principles are generally known in the art, but they bear repeating.

Figure 2:
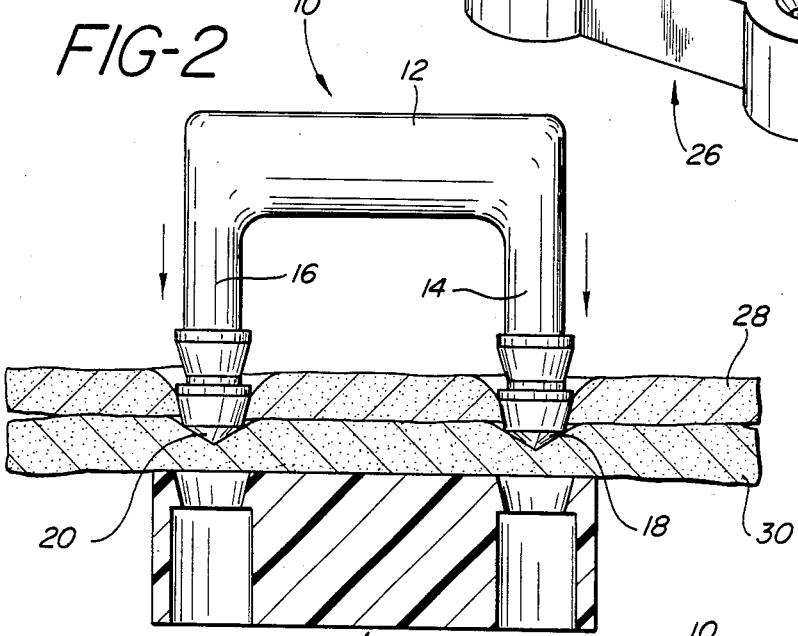
FIG. 2 is a front view of the staple of FIG. 1 in the act of fastening tissue.
Figure 3:
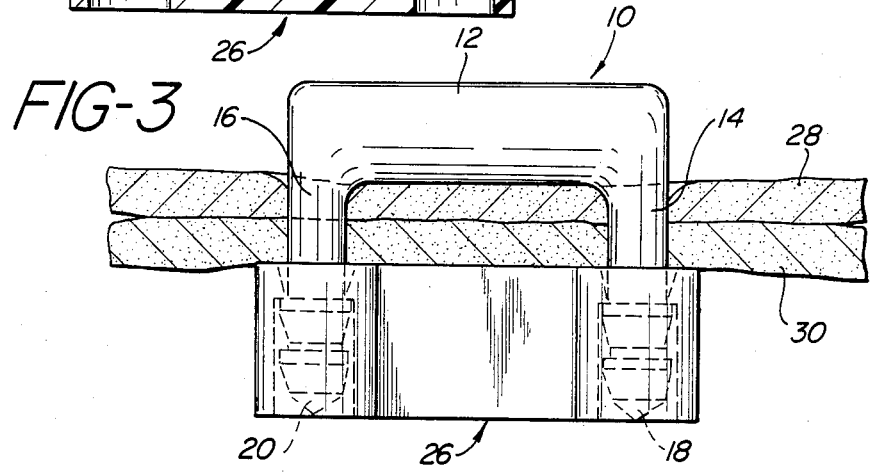
FIG. 3 is a front view of the staple of FIG. 1 in place holding tissue together.

FIGS. 1-3 show a typical staple of the invention. The fastener member 10 includes a base 12 and two legs 14,16 extending generally perpendicularly from the base 12. Each leg 14,16 has a pointed end 18,20 that is capable of piercing tissue. The legs 14,16 are arranged and constructed so as to snap fit into the receptacles 22,24 of a receiver 26. In a typical use, layers 28,30 of tissue to be fastened are positioned between the fastener member 10 and the receiver 26. The legs 14,16 of the fastener member 10 are driven through the layers 28,30 of tissue, as shown in FIG. 2, until the ends of the legs 14,16 snap fit in the receptacles 22,24 in the receiver 26, to thereby hold the tissue securely between the fastener member 10 and receiver 26, as is shown in FIG. 3. The design of fastener member and receiver shown in the figures is merely illustrative. Other designs can be used, if desired.

In another preferred aspect of the invention, there is provided a hemostatic or ligating clip comprising the blend of the invention. The advantages of the clip comprising the blend of the invention compared to clips made wholly of poly(p-dioxanone) are the following:

The lactide/glycolide copolymer component of the blend increases stiffness or rigidity so that, in many cases, the clip can be smaller than the prior known absorbable clips. The improved stiffness or rigidity permits the clip to be rigid enough to penetrate tissue (a penetrating clip is described below), so that the vessel to be ligated need not be isolated.

A ligating clip made from the lactide/glycolide copolymer alone would be dimensionally unstable at moderately elevated temperatures, and therefore would have to be shipped and stored under temperature-controlled conditions.

Figure 4:
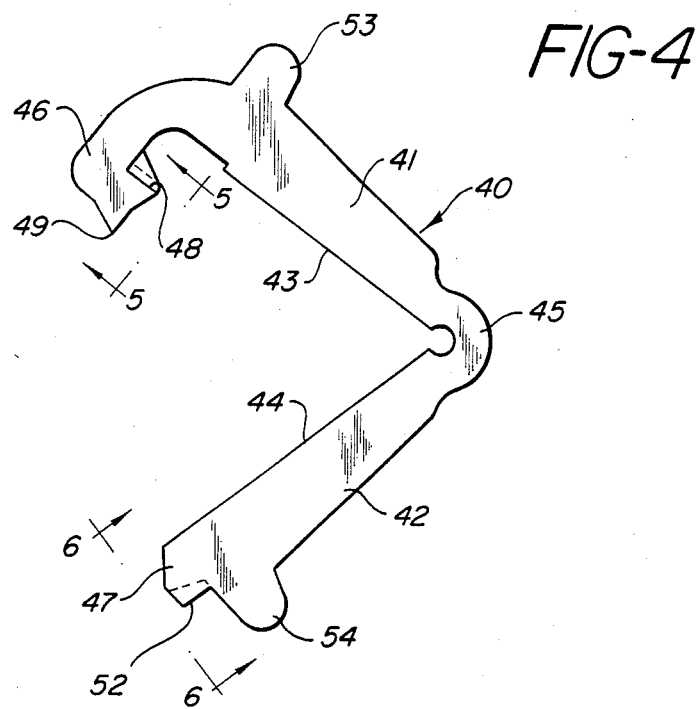
FIG. 4 is a perspective view of a ligating clip useful in the invention.

Referring to the drawings (FIGS. 4–9), there is shown a clip 40 that can be used in the invention. As depicted in FIG. 4, the clip comprises a pair of leg members 41 and 42 having opposed vessel clamping surfaces 43 and 44. The leg members are connected at their proximal ends by a resilient hinge portion 45.

Figure 5:
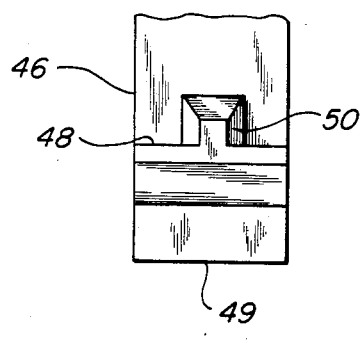
FIG. 5 is a front view taken along line 5—5 of FIG. 4.
Figure 6:
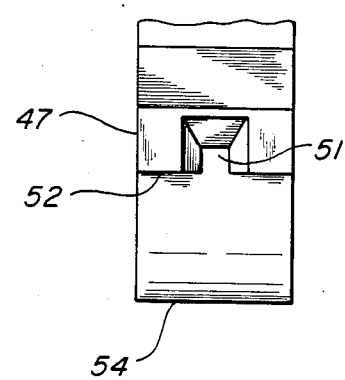
FIG. 6 is a front view taken along line 6—6 of FIG. 4.

The distal end of one of the leg members terminates in a return bend hook portion 46. The opposite leg member is somewhat shorter and terminates at its distal end in a portion 47 which can be grasped by the hook portion. The end of this leg member is angled at an obtuse angle to the vessel clamping surface. This angle aids in deflecting the hook portion as the two leg members are brought together about the hinge and allows the hook portion to deflect and then accept the leg member in the area between the inner surface 48 of the hook portion and the vessel clamping surface 43 of the opposite leg member. The hook portion includes a sharpened pointed end 49 extending from the hook portion and positioned to lead the hook portion or preceed the hook portion as the clip is being closed. As shown in FIG. 5, the hook portion has a protrusion 50 dispersed from the central portion of its inner surface 40. This protrusion fits into the recess 51 (see FIG. 6) positioned in the outer surface 52 of the opposite leg member 42. The protrusion and recess interlock when the clip is closed to prevent lateral movement of the leg members. The outside surfaces of the leg members each include a cylindrical boss 53 and 54 for use in holding the clip in a suitable instrument and applying the clip from said instrument as will hereinafter be described.

Figure 7:
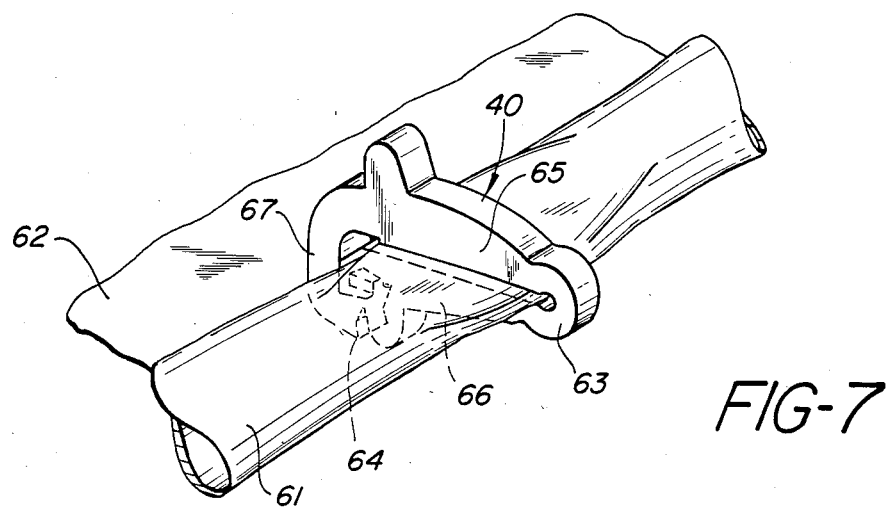
FIG. 7 is a perspective view of the clip depicted in FIG. 4 in a closed position about a blood vessel.
Figure 8:
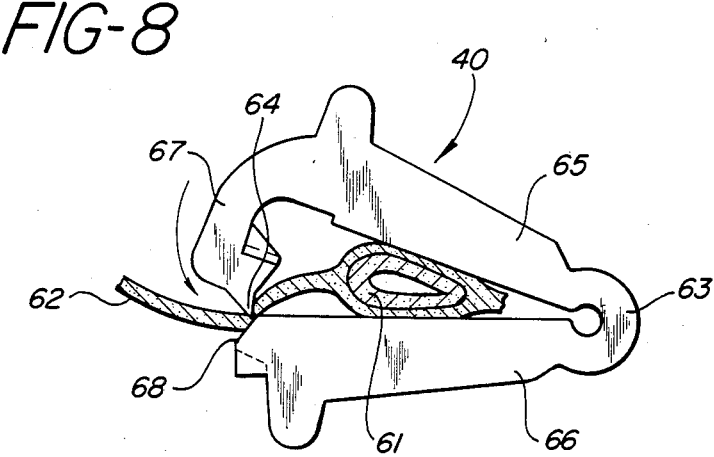
FIG. 8 is a side view of the clip of FIG. 4 immediately prior to the clip being closed about a vessel to be ligated.
Figure 9:
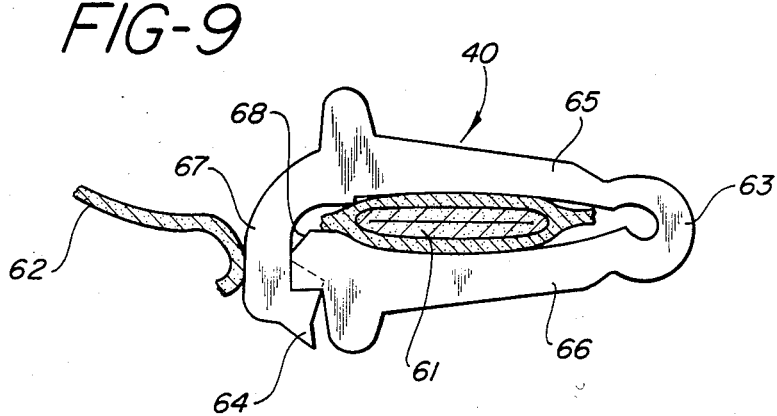
FIG. 9 is a side view of the clip of FIG. 4 with the clip in the fully closed position.

As may be more clearly seen in FIGS. 7, 8, and 9, when the clip 40 is clamped about a vessel 61 to be closed, assuming that the vessel has not been fully dissected from the surrounding connective tissue 62 (such as would be found in the mesentary), the vessel clamping surfaces are placed on opposite sides of the vessel and the leg members urged together about the resilient hinge. The penetrating sharpened end 64 of the one leg member 65 will pinch and scrape the connective tissue between itself and the camming surface 68 of the other leg member 66. This scraping action enhances the tissue penetrating ability of the sharpened end. Once the tissue is penetrated the usual sequence of closure takes place. As the leg members are urged closer together the leg member 66 continues to deflect the hook portion 67 and becomes engaged by the leg member 65, thereby locking the clip in place about the vessel without tissue interference with latch security. Though in the embodiment shown the penetrating means is a sharpened beveled end, the penetrating means may have other configurations such as a pointed end tapered at a plurality of sides, a pointed end, a plurality of pointed ends, etc.

Figure 10:
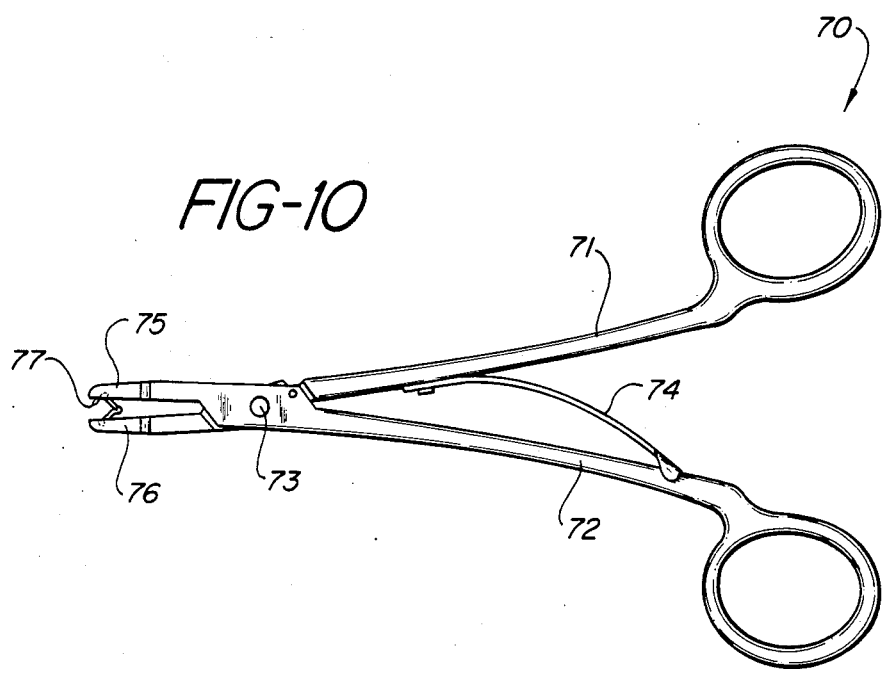
FIG. 10 is a side view of one type of instrument that may be used in applying the clip of FIG. 1.

In FIG. 10, there is shown a simplified drawing of an instrument for applying the clip described above. This instrument 70 comprises a pair of handles 71 and 72 which are connected together at a hinge point 73. The handles are biased with respect to one another by a spring 74. One of the handles extends beyond the hinge point in a first jaw member 75 and the opposite handle extends beyond the hinge point in a complementary second jaw member 76. The instrument engaging means comprises cylindrical bosses (53, 54 in FIG. 4) extending from the back surfaces of the leg members of the clip 77. These bosses fit into recesses in the jaws of the instrument.

The clip is placed in the jaws with the cylindrical bosses in the appropriate recesses. The vessel clamping surfaces of the clip are then placed on opposite sides of the vessel to be closed and the instrument handles urged together closing and locking the clip about the vessel and shutting off the vessel.

The clip can be injection molded by the procedure set forth above with respect to the fastener member of the staple of the invention.

After molding, the parts made of the blend of the invention are preferably annealed to impart dimensional stability (at elevated temperature) via crystallization. The annealing, which is preferably done in a vacuum or under an inert atmosphere such as nitrogen, can be carried out at about 60° to 90° C., and preferably at about 85° C., for at least an hour. An annealing time of about 2 to 20 hours is preferred.

EXAMPLES 1 AND 2 AND CONTROL EXAMPLE 1

A series of surgical staples having the design shown in FIGS. 1–3 were made by injection molding. The receivers were all made from poly(p-dioxanone) having an inherent viscosity of 1.6–1.8. The fasteners for the Example 1 and 2 staples were made from a blend of 30 weight percent poly(p-dioxanone) having an inherent viscosity of 1.6–1.8 and 70 weight percent of an 85/15 (mol/mol) lactide/glycolide copolymer having an inherent viscosity of 2.76 (Example 1) or 1.76 (Example 2). The melt blends were made using an extruder equipped with a mixing head, which extruded a rod that was fed to a pelletizer and chopped up into pellets. The fasteners for Control Example 1 were made from the pure copolymer having an inherent viscosity of 1.6–1.8.

Prior to injection molding, the polymers and polymer melt blends, in pellet form, were dried under vacuum for a period of two weeks. Dryness was maintained during molding by using a dry nitrogen purge in the hopper of the injection molding machine. After molding, the samples were maintained under vacuum or under a dry nitrogen purge until they were tested. The fasteners of Examples 1 and 2 were annealed at 85° C. (185° F.) for 16 hours after molding. (The control was not annealed because the elevated temperature would have destroyed the part.)

The samples were tested by placing them in aqueous phosphate buffer solution (pH=7.2) at 37° C. Samples were removed at seven-day intervals and tested on an Instron tensiometer to measure the amount of force required to separate the fastener from the receiver. The results are displayed below in Table I:

TABLE I

| Sample | Separation Force, Lbs. | | | | | | |
|---|---|---|---|---|---|---|---|
| | Initial | 7 Day | 14 Day | 21 Day | 28 Day | 35 Day | 42 Day |
| Example 1 | 8.36 | 4.73 | 2.75 | 2.2 | 2.47 | 2.11 | 2.12 |
| BSR[1] | 100 | 57 | 33 | 26 | 30 | 25 | 25 |
| Example 2 | 8.26 | 2.46 | 1.44 | 1.27 | 1.72 | 1.22 | 1.3 |
| BSR | 100 | 30 | 17 | 15 | 21 | 15 | 16 |
| Control 1 | 7.05 | 6.91 | 7.62 | 5.91 | 6.45 | 5.11 | 3.3 |
| BSR | 100 | 98 | 108 | 84 | 91 | 72 | 47 |

[1] % Breaking Strength retention.

The Control exhibits a higher separation force for two reasons; first, this copolymer swells when subjected to the buffer solution, and thereby increases the system's resistance to separation; and, second, the absorption time would be slightly longer than with the blend of the invention. The staples of the invention, as illustrated by Examples 1 and 2, exhibit acceptable separation force values for the surgical applications they are being considered for. The Control does exhibit higher separation force values than the Examples, but the higher values are not mandatory considering the length of time required for healing of tissue involved in surgery.

The major benefit of the polymer blend system when used in the fastener member of a fastener/receiver type staple, which benefit is not readily apparent from the above Examples, is that the Control system copolymer cannot be subjected to moderately elevated temperature without incurring significant dimensional instability. The Examples, 1 and 2, were subjected to elevated temperature (in the annealing step) prior to the separation force testing, and they exhibited excellent dimensional stability and acceptable in vitro strength retention performance. As indicated earlier, dimensional stability at elevated temperatures is absolutely necessary if a part made from an absorbable polymer is to be safely transported where the container of parts, or the truck, train, etc., in which the container is carried, is exposed to high ambient temperature such as is found throughout the United States in the warmer months. Dimensional instability is impermissible in a part that is to be used in a critical medical or surgical procedure.

What is claimed is:

1. A surgical fastener comprising a blend of a copolymer containing from about 65 to about 90 mol percent lactide and from about 10 to about 35 mol percent glycolide, and poly(p-dioxanone), said blend containing from about 25 to about 50 weight percent poly(p-dioxanone), the remainder comprising said copolymer.

2. The surgical fastener of claim 1 in the form of a staple comprising:
   (a) a fastener member including a base member and at least one leg member terminating in a pointed free end, said leg member extending substantially perpendicularly from said base member; and
   (b) a receiving member including at least one aperture arranged and constructed to receive and retain the free end of said leg member, wherein said fastener member comprises a blend of a copolymer containing from about 65 to about 90 mole percent lactide and from about 10 to about 35 mole percent glycolide, and poly(p-dioxanone), said blend containing from about 25 to about 50 weight percent poly(p-dioxanone), the remainder comprising said copolymer, and wherein said receiving member is an absorbable polymer.

3. The surgical fastener of claim 2 wherein said absorbable polymer is poly(p-dioxanone).

4. The surgical fastener of claim 2 wherein said copolymer contains about 85 mole percent polymerized lactide, the remainder being polymerized glycolide, and wherein said blend contains about 70 weight percent of said copolymer, the remainder comprising poly(p-dioxanone).

5. The surgical fastener of claim 3 wherein said copolymer contains about 85 mole percent polymerized lactide, the remainder being polymerized glycolide, and wherein said blend contains about 70 weight percent of said copolymer, the remainder comprising poly(p-dioxanone).

6. The surgical fastener of claim 1 in the form of a ligating clip.

7. The surgical fastener of claim 1 in the form of an anastomotic coupler.

8. The surgical fastener of claim 1 in the form of a fascia closure.

* * * * *